(12) United States Patent  (10) Patent No.: US 7,485,404 B2
Chichiishi et al.  (45) Date of Patent: Feb. 3, 2009

(54) NONSOLVATE-FORM CRYSTAL OF POLYMETHINE COMPOUND AND PROCESS FOR PRODUCING THE SAME

(75) Inventors: Keiki Chichiishi, Yao (JP); Sayuri Wada, Yao (JP); Shigeo Fujita, Yao (JP)

(73) Assignee: Yamamoto Chemicals, Inc., Yao-shi (JP)

( * ) Notice: Subject to any disclaimer, the term of this patent is extended or adjusted under 35 U.S.C. 154(b) by 269 days.

(21) Appl. No.: 10/579,142
(22) PCT Filed: Nov. 12, 2004
(86) PCT No.: PCT/JP2004/016830
§ 371 (c)(1),
(2), (4) Date: May 15, 2006
(87) PCT Pub. No.: WO2005/049736
PCT Pub. Date: Jun. 2, 2005

(65) Prior Publication Data
US 2007/0083048 A1  Apr. 12, 2007

(30) Foreign Application Priority Data
Nov. 21, 2003 (JP) ............ 2003-392789

(51) Int. Cl.
G03F 7/00 (2006.01)
G03F 7/004 (2006.01)
(52) U.S. Cl. .................. 430/270.1; 430/270.15; 430/944
(58) Field of Classification Search .............. 430/270.1, 430/270.15, 944
See application file for complete search history.

(56) References Cited

U.S. PATENT DOCUMENTS 4,973,572 A * 11/1990 DeBoer .................. 503/227
5,386,058 A *  1/1995 Mader .................... 564/330

FOREIGN PATENT DOCUMENTS

EP           1074889 A2 *  2/2001

(Continued)

Primary Examiner—Amanda C. Walke
(74) Attorney, Agent, or Firm—Birch, Stewart, Kolasch & Birch, LLP

(57) ABSTRACT

A novel nonsolvate-form crystal of polymethine compound is provided which has good stability in solution, shows a high gram extinction coefficient, is excellent in storage stability, is easy to handle and is highly sensitive to general-purpose semiconductor lasers.

Thus is provided a nonsolvate-form crystal of polymethine compound of the formula (I) given below as well as a process for producing the nonsolvate-form crystal of polymethine compound of formula (I) which comprises reacting a polymethine ether compound of the formula (II) given below with hydrochloric acid or hydrobromic acid.

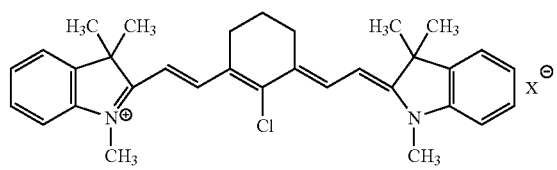

(In the above formula, X represents Cl or Br.)

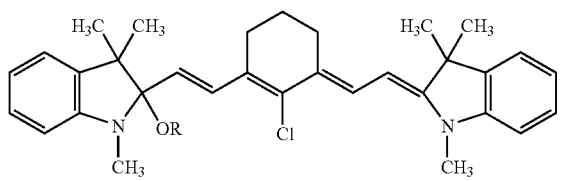

(In the above formula, R represents an alkyl group, an alkoxyalkyl group or an optionally substituted aryl group.)

10 Claims, 10 Drawing Sheets

FOREIGN PATENT DOCUMENTS

| | | | |
|---|---|---|---|
| EP | 1101607 A1 * | 5/2001 | |
| JP | 2002-356069 A | 12/2002 | |
| JP | 2004029191 A * | 1/2004 | |
| WO | WO-01/07524 A1 | 2/2001 | |
| WO | WO-2005/000814 A1 | 1/2005 | |

* cited by examiner

NONSOLVATE-FORM CRYSTAL OF POLYMETHINE COMPOUND AND PROCESS FOR PRODUCING THE SAME

TECHNICAL FIELD

The present invention relates to a novel nonsolvate-form crystal of a polymethine compound, a process for producing the same, and a near-infrared absorbing material using the nonsolvate-form crystal.

BACKGROUND ART

In recent years, polymethine compounds have come into wide use, among others, as materials for optical recording media and near-infrared absorbing filters, or as light-to-heat converting agents in materials for plate making utilizing laser beams. In the field of materials for plate making utilizing laser beams, in particular, the demand for compounds which are highly sensitive to laser beams emitted by general-purpose semi-conductor lasers, for example in the laser wavelength range of 780 nm to 830 nm, and are fairly soluble in general-purpose solvents, for example alcohols such as methanol and ethanol, has recently been increasing. Further, it is also important that such compounds be stable and easy to handle and free of impurities possibly producing adverse effects in various fields of application. However, any polymethine compound capable of satisfying such requirements is not known.

Since certain polymethine compounds were disclosed in Zh. Org. Khim. (1978), 14 (10), various investigations have been made concerning compounds similar in structural formula itself to the polymethine compounds of the present invention. According to the known methods of synthesizing such compounds, an indolenium compound represented by the formula (III)

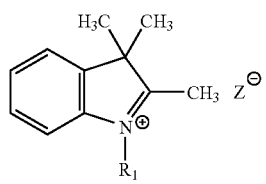

(III)

wherein $R_1$ represents an alkyl group, which may optionally be substituted, and Z represents an acidic residue, or an indoline compound represented by the general formula (IV)

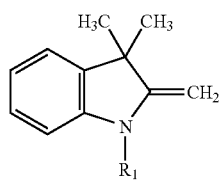

(IV)

wherein $R_1$ represents an alkyl group, which may optionally be substituted, for instance, is condensed with a diformyl compound represented by the formula (V) or a dianil compound represented by the formula (VI)

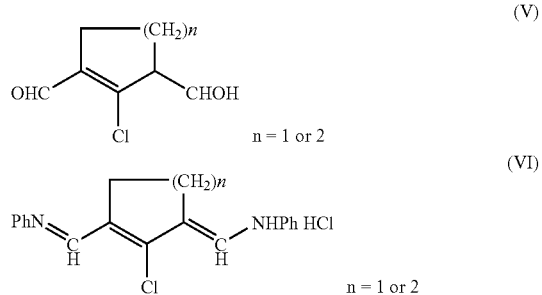

in a dehydrating organic acid in the presence of a fatty acid salt (cf. e.g. WO 01/07524; Japanese Kokai Publication H10-195319, pages 8-10; J. Org. Chem. 1995, 60, 2394; Japanese Patent Specification No. 3045404, Example 1; German Laid-open Patent Specification DE 3721850; Japanese Kokai Publication S62-36469).

Among them, the method of synthesizing polymethine compounds by reacting an indolenium compound of formula (III) with a dianil compound of formula (VI) is the commonest. In that case, however, the acidic residue $Z^-$ is limited in kind from the viewpoint of reaction yield of the product polymethine compound and ease of operation in isolation and purification, among others. Such method is generally used in producing polymethine compounds in which Z is the perchloric acid residue, tetrafluoroboric acid residue or p-toluenesulfonic acid residue. Those cases where $Z^-$ is a halogen ion other than $I^-$, in particular where $Z^-$ is $Cl^-$ or $Br^-$, are not yet known.

As for the method comprising reacting an indoline compound of formula (IV) with a diformyl compound of formula (V), a synthesis example in which the counter ion to a polymethine compound is $Cl^-$ is disclosed in German Laid-open Patent Specification DE 3721850 (in Example 1). However, the compound obtained by the method of synthesis described in this document differs in structural formula from the polymethine compound of the present invention and no other physical characteristic values than the maximum absorption wavelength ($\lambda$max) are described in that document. When a compound having the same structure as that of a polymethine compound (X=Cl) of the present invention was produced by the production method disclosed there, the yield was low and the compound obtained was low in purity and in a hydrated form. Further, the diformyl compound of formula (V) as used therein is poor in storage stability and hazardous (positive in mutagenecity testing) and, therefore, caution is necessary in handling the same and the use thereof as a raw material for commercial scale production is undesirable.

WO 01/07524 discloses, in Example 1, an example of synthesis of a compound whose basic structural formula is the same as that of the polymethine compound of the invention in which the counter ion is $Br^-$. Therefore, the present inventors attempted to synthesize the compound identical in structure to the polymethine compound of the present invention in accordance with the method disclosed in WO 01/07524. However, the compound obtained was in a hydrated form and low in purity and, therefore, the use thereof is greatly restricted, for example it cannot be used in systems on which water exerts an adverse influence.

As for the method comprising reacting an indoline compound of formula (IV) with a dianil compound of formula (VI), Japanese Kokai Publication S62-36469 discloses, in Example 3, an example of the production of a compound differing in basic structural formula from the polymethine compound of the present invention but having Cl⁻ as Z⁻. When a compound structurally identical to the polymethine compound (X=Cl) of the present invention was produced by the production method disclosed there, the substance obtained was a methanol adduct and was a low-purity compound.

Further, a recent Japanese edition of Aldrich Comprehensive Reagent Catalog (2003-2004) describes a compound (X being Cl) identical in structural formula to the polymethine compound of the present invention. However, this substance is a hydrate and is a compound very low in purity and, therefore, the use thereof is greatly restricted, for example it cannot be used in systems on which water exerts an adverse influence.

The term "solvate" as used herein is a generic one including the hydrate.

As described above, the known compound identical in structural formula to the compound of the invention occurs as a solvate due to the process for production thereof and is a low-purity product and, therefore, the use thereof is greatly restricted. When the solvate-form compound structurally identical to the compound of the present invention is used as a light-to-heat converting agent in plate making by the CTP (computer-to-plate) technique, difficulties are encountered, namely the solution stability is poor, and the light-to-heat conversion efficiency widely fluctuates due to the fact that the purity is not constant.

Meanwhile, no report can be found about the fact that in the case of polymethine compounds, there are great differences in stability in solution and in sensitivity between the solvated form and non-solvated form in spite of the same basic structure of the compound.

DISCLOSURE OF INVENTION

Problems Which the Invention is to Solve

It is an object of the present invention to provide a novel nonsolvate-form crystal of a polymethine compound, which is very stable in solution, shows a high gram extinction coefficient, is highly pure, stable and easy to handle and is highly sensitive to beams emitted by general-purpose semiconductor lasers.

Means for Solving the Problems

The present inventors made various investigations in an attempt to solve the problems discussed above and, as a result, found that a novel nonsolvate-form crystal of a compound having a specific structure shows good stability in solution and a high gram extinction coefficient, is highly sensitive to laser beams around 780 nm to 830 nm and highly pure and stable and can be used as a near-infrared absorbing material readily processable in various fields of application. Based of such and other findings, they have now completed the present invention.

Thus, in a first aspect, the invention provides a nonsolvate-form crystal of a polymethine compound represented by the formula (I):

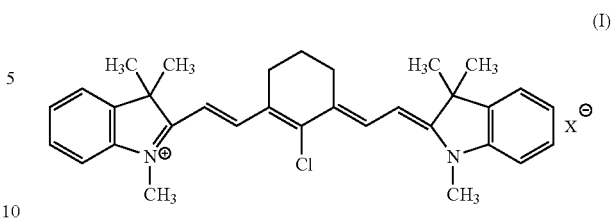

wherein X represents Cl or Br.

The nonsolvate-form crystal of polymethine compound of the present invention, when X is Cl, has a melting point (decomposition temperature) of not lower than 205° C. and, when X is Br, it has a melting point (decomposition temperature) of not lower than 220° C. and, in TG-DTA (thermogravimetry-differential thermal analysis) charts, both crystal forms show weight losses not exceeding 3% at 150° C. and below and, therefore, they are substantially in non-solvated form.

Furthermore, when X is Cl, the crystal form is characterized by a powder X-ray diffraction pattern showing characteristic peaks at diffraction angles (2θ±0.2°) of 11.2°, 16.7°, 24.2° and 25.3° in powder X-ray diffraction using the Cu-Kα rays. When X is Br, the crystal form is characterized by a powder X-ray diffraction pattern showing characteristic peaks at diffraction angles (2θ±0.2°) of 17.0°, 20.5°, 21.1° and 24.9° in powder X-ray diffraction using the Cu-Kα rays.

In a second aspect, the present invention provides a process for producing a nonsolvate-form crystal of polymethine compound represented by the formula (I) given above which process is characterized in that a polymethine ether compound represented by the formula (II)

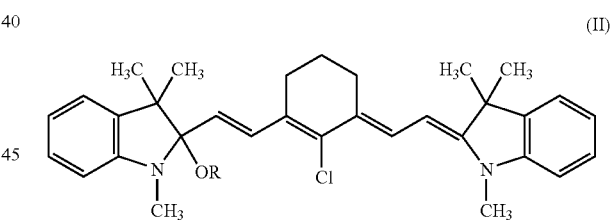

wherein R represents an alkyl group, and alkoxyalkyl group or an optionally substituted aryl group, with hydrochloric acid or hydrobromic acid.

In a third aspect, the present invention provides a near-infrared absorbing material which comprises a nonsolvate-form crystal of polymethine compound of formula (I).

DETAILED DESCRIPTION OF THE INVENTION

Figure 1:
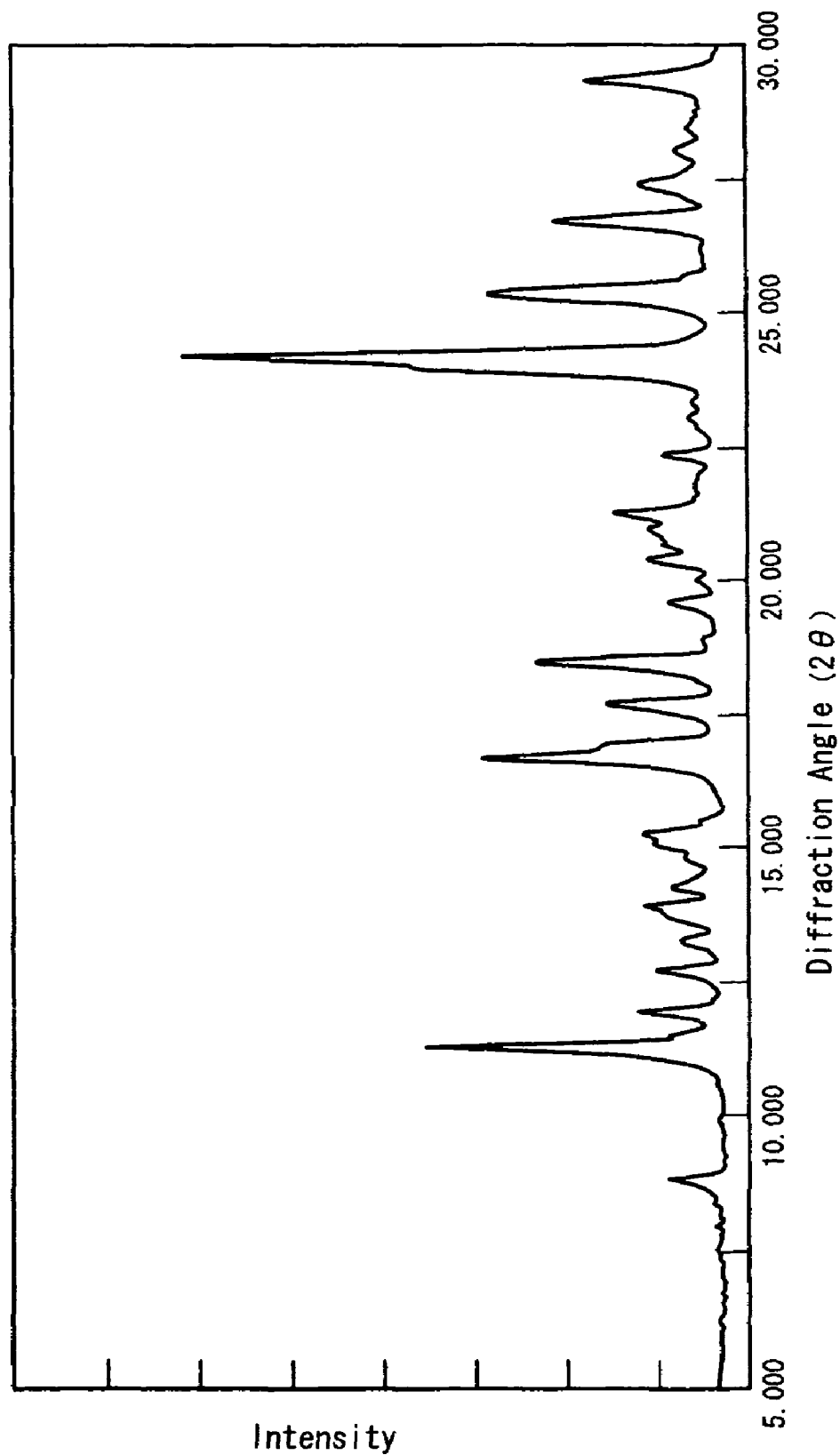
FIG. 1 is a powder X-ray diffraction pattern of the polymethine compound of Example 1.

In the following, the invention is described in detail.

The known compound represented by the chemical structural formula (I) or the compounds of formula (I) as obtained by the known production methods are substances solvated with water or an organic solvent (e.g. methanol, ethanol) and, in most cases, are low in purity. On the contrary, the nonsolvate-form crystal of polymethine compound of the invention as represented by the formula (I) is in a quite novel crystal form not solvated with water or any organic solvent.

The nonsolvate-form crystal of polymethine compound of the invention which is represented by the formula (I), when X is Cl, has a melting point (decomposition temperature) of not lower than 205° C., preferably 210° C. to 240° C. The solvate form and/or low purity products have a melting point lower than 205° C.

The nonsolvate-form crystal of polymethine compound of the invention which is represented by the formula (I), when X is Br, has a melting point (decomposition temperature) of not lower than 215° C., preferably 220° C. to 250° C. The solvate form and/or low purity products have a melting point lower than 215° C.

Both the nonsolvate-form crystals of the invention, after starting melting, gradually foam and decompose, so that the melting points (decomposition temperatures) can be observed very clearly. The solvate form and/or low purity products do not show any definite melting point or decomposition temperature in some instances.

The TG-DTA (thermogravimetry-differential thermal analysis) charts of the nonsolvate-form crystal of polymethine compounds of the invention as represented by the formula (I) show a weight loss in TG of not greater than 3%, preferably not greater than 2%, at 150° C. and below. In the case of the solvate form and/or low purity products, the weight loss in TG is greater than 3% at 150° C. and below.

In powder X-ray diffraction using the Cu-Kα rays, the nonsolvate-form crystal of polymethine compound of the invention as represented by the formula (I), when X is Cl, shows characteristic peaks at diffraction angles (2θ±0.2°) of 11.2°, 16.7°, 24.2° and 25.3°, preferably of 11.2°, 16.7°, 18.5°, 24.2°, 25.3° and 26.7°. When X is Br, it shows characteristic peaks at diffraction angles (2θ±0.2°) of 17.0°, 20.5°, 21.1° and 24.9°, preferably of 9.6°, 17.0°, 20.5°, 21.1°, 24.9° and 27.4°. The solvate form and/or low purity products show quite different powder X-ray diffraction patterns.

It has been revealed that the nonsolvate-form crystal of polymethine compound of the invention can be produced only via (by using as the raw material) the polymethine ether compound represented by the formula (II).

Surprisingly, the nonsolvate-form crystal of polymethine compound of the invention as represented by the formula (I) is higher in solution stability in alcohol solvents, such as methanol and ethanol, and ketone solvents, such as acetone and methyl ethyl ketone, which are used in the field of laser thermal recording materials where laser beams are utilized, as compared with the known solvated compounds, hence it is very suited for use in this field of application. Further, it shows a high extinction coefficient in the region of 780-830 nm and therefore can be properly used in a number of recoding material fields where laser beams, in particular laser beams in the range of 780-830 nm as emitted by general-purpose semiconductor lasers, are utilized; further, it is very useful in the field of such recording materials as laser thermal transfer recording materials and laser thermal recording materials, and in the field of plate making materials.

[Process for Producing the Nonsolvate-Form Crystal of Polymethine Compound]

The nonsolvate-form crystal of polymethine compound of the invention as represented by the formula (I) can be produced by the following method.

It can be produced by reacting a polymethine ether compound (e.g. R=CH₃) of the general formula (II) given below with hydrochloric acid or hydrobromic acid in an organic solvent.

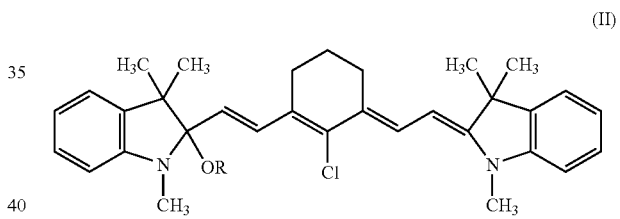

(II)

wherein R represents an alkyl group, an alkoxyalkyl group or an optionally substituted aryl group.

When R is an alkyl group, it is preferably a straight or branched alkyl group containing 1-8 carbon atoms, particularly preferably a straight or branched alkyl group containing 1-4 carbon atoms. As examples, there may be mentioned methyl, ethyl, n-propyl, isopropyl, n-butyl, isobutyl, sec-butyl, tert-butyl, n-pentyl, isopentyl, n-hexyl, isohexyl, sec-hexyl, 2-ethylbutyl, n-heptyl, isoheptyl, sec-heptyl, n-octyl and 2-ethylhexyl.

When R is an alkoxyalkyl group, it is preferably one containing 2-8 carbon atoms in total, particularly preferably one containing 2-4 carbon atoms in total. As example, there may be mentioned methoxymethyl, 2-methoxyethyl, 3-methoxypropyl, ethoxymethyl, 2-ethoxyethyl, 2-propoxyethyl and 2-butoxyethyl.

When R is an optionally substituted aryl group, it may be an optionally substituted phenyl group or an optionally substituted naphthyl group but preferably is an optionally substituted phenyl group. Each substituent may be an alkyl, amino, nitro, alkoxy or hydroxy group or a halogen atom, and preferably is an alkyl group containing 1-4 carbon atoms or an alkoxy group containing 1-4 carbon atoms.

As examples of R when it is an alkyl-substituted phenyl, there may be mentioned 2-methylphenyl, 3-methylphenyl, 4-methylphenyl, 2,3-dimethylphenyl, 2,4-dimethylphenyl, 3,4-dimethylphenyl, 2,5-dimethylphenyl, 2,6-dimethylphenyl, 2-ethylphenyl, 3-ethylphenyl, 4-ethylphenyl, 2,3-diethylphenyl, 2,4-diethylphenyl, 3,4-diethylphenyl, 2,5-diethylpehnyl and 2,6-diethylphenyl.

As examples of R when it is an alkoxy-substituted phenyl, there may be mentioned 2-methoxyphenyl, 3-methoxyphenyl, 4-methoxyphenyl, 2,3-dimethoxyphenyl, 2,4-dimethoxyphenyl, 3,4-dimethoxyphenyl, 2,5-dimethoxyphenyl and 2,6-dimethoxyphenyl.

The organic solvent includes alcohols such as methanol, ethanol, n-propanol, isopropanol and n-butanol, ketones such as acetone, methyl ethyl ketone, methyl propyl ketone and methyl butyl ketone, ethers such as tetrahydrofuran and dioxane, esters such as methyl acetate, ethyl acetate and butyl acetate, aromatic hydrocarbons such as benzene, toluene and xylene, halogenated hydrocarbons such as dichloromethane, trichloromethane, dichloroethane and trichioroethane, and aprotic polar solvents such as dimethylformamide, dimethylacetamide and dimethyl sulfoxide. Particularly preferred are alcohols such as methanol, ethanol, n-propanol, isopropanol and n-butanol, ketones such as acetone, methyl ethyl ketone, methyl propyl ketone and methyl butyl ketone, and esters such as methyl acetate, ethyl acetate and butyl acetate.

As for the quantity proportion between the compound represented by the formula (II) and hydrochloric acid or hydrobromic acid, the latter is used generally in an amount of about 0.5 to 3 moles, preferably about 1 to 1.5 moles, per mole of the former.

The organic solvent is used generally in an amount of about 1 to 30 liters, preferably about 3 to 20 liters, per mole of the compound represented by the formula (II).

Generally, the above-mentioned reaction proceeds smoothly at a temperature not higher than 100° C., preferably between 10-70° C., and generally will be complete in about several minutes to 5 hours.

After reaction, the desired product can be isolated with ease by filtration and washing. It can be purified with ease by any of conventional means of purification, for example recrystallization.

Usable as the solvent for isolation and purification are conventional organic solvents, for example alcohols such as methanol, ethanol, n-propanol, isopropanol and n-butanol, ketones such as acetone, methyl ethyl ketone, methyl propyl ketone and methyl butyl ketone, ethers such as tetrahydrofuran and dioxane, esters such as methyl acetate, ethyl acetate and butyl acetate, aromatic hydrocarbons such as benzene, toluene and xylene, halogenated hydrocarbons such as dichloromethane, trichloromethane, dichloroethane and trichloroethane, and aprotic polar solvents such as dimethylformaide, dimethylacetamide and dimethyl sulfoxide. Preferred are ketone solvents such as acetone, methyl ethyl ketone, methyl propyl ketone and methyl butyl ketone, and ester solvents such as methyl acetate, ethyl acetate and butyl acetate, and mixture of these. When such solvents as methanol, ethanol and toluene, for instance, are used, salvation may occur under certain isolation conditions.

The polymethine ether compound (II) mentioned above can be prepared, for example, by reacting a polymethine compound represented by the formula (VII) given below with an alkali metal alkoxide or alkali metal aryloxide represented by the formula (VIII) given below in an organic solvent.

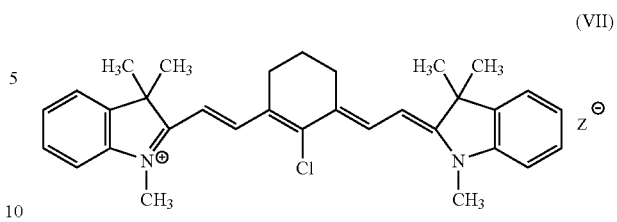

(VII)

(In the formula, $Z^-$ represents an acidic residue.)

MOR (VIII)

(In the formula, M represents an alkali metal and R is as defined above.)

In the above formula, $Z^-$ represents an acidic residue, for example $F^-$, $Cl^-Br^-$, $I^-$, $BrO_4^-$, $ClO_4^-$, $BF_4^-$, $PF_4^-$, $SbF_6^-$, $CF_3CO_2^-$, $CH_3CO_2^-$, $CF_3SO_3^-$, $CH_3SO_3^-$, benzenecarbonato, benzenesulfonato, p-toluenesulfonato (hereinafter referred to as $TsO^-$ for short), naphthalenecarbonato, naphthalenedicarbonato, naphthalenesulfonato, naphthalenedisulfonato or the like. In particular, $Cl^-Br^-$, $I^-$, $ClO_4^-$, $BF_4^-$, $PF_4^-$, $SbF_6^-$, $CF_3CO_2^-$, $CF_3SO_3^-$, $CH_3SO_3^-$, benzenecarbonato, benzenesulfonato and $TsO^-$ are preferred, and $ClO_4^-$, $BF_4^-$ and $TsO^-$ are more preferred.

In the above reaction, such an alkali metal as sodium or potassium is used as M.

As the organic solvent, there may be mentioned alcohols such as methanol, ethanol, n-propanol, isopropanol and n-butanol, ethers such as tetrahydrofuran and dioxane, esters such as methyl acetate, ethyl acetate and butyl acetate, aromatic hydrocarbons such as benzene, toluene and xylene, halogenated hydrocarbons such as dichloromethane, trichloromethane, dichloroethane and trichioroethane, and aprotic polar solvents such as dimethylformamide, dimethylacetamide and dimethyl sulfoxide.

As for the proportion between the compound represented by the general formula (VII) and the compound represented by the general formula (VIII), the latter is used generally in an amount of about 1-30 moles, preferably about 2-10 moles, per mole of the former.

The organic solvent is used generally in an amount of about 2-30 liters, preferably about 5-20 liters, per mole of the compound represented by the general formula (VII).

Generally, the above reaction proceeds smoothly at a temperature of about 0-100° C., preferably at 10-70° C., and generally will be complete in about several minutes to 10 hours.

After reaction, the desired product can be isolated with ease by filtration and washing. It can be purified with ease by any of conventional means of purification, for example recrystallization or column separation.

The compound represented by the general formula (VII) can be synthesized by the method described in Japanese Kokai Publication 2000-226528, for instance.

[Near-Infrared Absorbing Material]

As for the near-infrared absorbing material, the nonsolvate-form crystal of polymethine compound of formula (I) may be used singly or in combination with an appropriate binder resin, another near-infrared absorbing substance, a color-forming component, a coloring component and/or the like, according to need.

The binder resin is not particularly restricted but includes homopolymers and copolymers of acrylic monomers such as acrylic acid, methacrylic acid, acrylic esters, methacrylic esters, etc.; cellulosic polymers such as methylcellulose, ethylcellulose, cellulose acetate, etc.; vinyl polymers and vinyl compound copolymers such as polystyrene, vinyl chloride-vinyl acetate copolymer, polyvinylpyrrolidone, polyvinyl butyral, polyvinyl alcohol, etc.; condensation polymers such as polyesters and polyamides, rubber type thermoplastic polymers such as butadiene-styrene copolymer, and polymers produced by the polymerization and crosslinking of photopolymerizable compounds such as epoxy compounds, among others.

The near-infrared absorbing substance to be used in the near-infrared absorbing material may comprise not only the non-solvate-form crystal of polymethine compound of general formula (I) but also any of various known near-infrared absorbing substances unless the latter defeats the object of the present invention.

The near-infrared absorbing substances which can be used concomitantly include not only the common pigments, such as carbon black and aniline black, but also the various pigment type and dye type colors described in Near-Infrared Absorbing Colors (p. 45-51) in "Kagaku Kogyo (Chemical Industry)", May, 1986 issue and "Development and Market Trend of Functional Colors in the Nineties", CMC (1990), Chapter 2-2.3., such as polymethine colors (cyanine colors), phthalocyanine colors, dithiol metal complex salt colors, naphthoquinone and anthraquinone colors, triphenylmethane (analogous) colors, aminium and diimmonium colors, etc., as well as azo colors, indoaniline metal complex colors, intermolecular CT colors and so forth.

In cases where the near-infrared absorbing material of the present invention is used as a light-to-heat converting agent in materials for plate making utilizing laser beams, original plates for plate making can be produced by applying a solution of the nonsolvate-form crystal of polymethine compound represented by the formula (I) in an organic solvent to supports, for example paper sheets, plastic (e.g. polyethylene, polypropylene, polystyrene)-laminated paper sheets, plates or sheets of a metal such as aluminum (including an aluminum alloy), zinc or copper, or plastic films made of cellulose diacetate, cellulose triacetate, cellulose butyrate, polyethylene terephthalate, polyethylene, polystyrene, polypropylene, polycarbonate, polyvinyl acetal or the like. The solvent to be used in the solution to be applied is not particularly restricted but includes, among others, hydrocarbons, halogenated hydrocarbons, ethers, ketones, alcohols and cellosolves. Preferred are, however, ethers such as tetrahydrofuran and dioxane, ketones such as methyl ethyl ketone, methyl isobutyl ketone and cyclohexanone, alcohol solvents such as methanol, ethanol and propanol, and cellosolve solvents such as methylcellosolve and ethylcellosolve. Particularly preferred are ketones such as methyl ethyl ketone, methyl isobutyl ketone and cyclohexanone, and alcohol solvents such as methanol, ethanol and propanol.

In using the near-infrared absorbing material of the invention in a recording material such as a laser thermal transfer recording material or a laser thermal recording material, the crystal of polymethine compounds represented by the formula (I) in nonsolvate-form may be used as formulated with a color-forming component or a color component, or a discrete layer containing a color-forming component or a color component may be provided. As the color-forming component or color component, sublimable dyes or pigments, electron-donating dye precursor-electron-accepting compound systems, and the systems heretofore explored in which images are formed by heat-induced physicochemical changes in polymerizable polymers or the like can be employed.

For example, the color component of a laser thermal transfer recording material is not particularly restricted but, as pigment type components, there can be mentioned inorganic pigments such as titanium dioxide, carbon black, zinc oxide, Prussian blue, cadmium sulfide, iron oxide, chromates of lead, zinc, barium and calcium, etc., and organic pigments such as azo, thioindigo, anthraquinone, anthanthrone, triphenodioxazine, phthalocyanine, quinacridone and other pigments. The dye which can be used includes acid dyes, direct dyes, disperse dyes, oil-soluble dyes and metal-containing oil-soluble dyes, among others.

The color-forming component for a laser thermal recording material is not particularly restricted but the substances which have heretofore been utilized in thermal recoding materials can be employed. As electron-donating dye precursor, there is employed a compound having a partial skeleton in the form of a lactone, lactam, sultone, spiropyran, ester, amide, or the like, and developing color by giving off an electron or receiving a proton, for example from an acid, with said partial skeleton being opened or cleaved on contact with an electron-accepting compound. For example, there can be mentioned triphenylmethane compounds, fluoran compounds, phenothiazine compounds, indolylphthalide compounds, leucoauramine compounds, rhodamine-lactam compounds, triphenylmethane compounds, triazene compounds, spiropyran compounds, fluorene compounds and so forth. As the electron-accepting compound, there can be mentioned phenolic compounds, organic acids or metal salts thereof, and hydroxybenzoic esters, among others.

When the near-infrared absorbing material of the invention is used in near-infrared absorbing filters, heat ray shielding materials or films for agricultural use, the nonsolvate-form crystal of polymethine compound represented by the formula (I) is admixed with a plastic resin, if necessary together with an organic solvent, and the mixture can be molded into sheets or films by various methods so far investigated in the art, for example by injection molding or casting. The resin that can be used is not particularly restricted but includes, among others, acrylic resins, polyethylene resins, vinyl chloride resins, vinylidene chloride resins and polycarbonate resins. The solvent to be used is not particularly restricted but includes, for example, hydrocarbons, halogenated hydrocarbons, ethers, ketones, alcohols and cellosolves. Alcohols such as methanol, ethanol and propanol and cellosolve solvents such as methylcellosolve and ethylcellosolve, in particular, are preferred.

When the near-infrared absorbing material of the present invention is used in such optical recording materials as optical cards, a solution is prepared by dissolving the nonsolvate-form crystal of polymethine compound represented by the formula (I) in an organic solvent, and the solution can be applied to such substrates as glass or plastic resin substrates by any of various techniques so far investigated, for example by spin coating. The resin that can be used as the substrate resin is not particularly restricted but includes, among others, acrylic resins, polyethylene resins, vinyl chloride resins, vinylidene chloride resins and polycarbonate resins. The solvent to be used in spin coating is not particularly restricted but includes, for example, hydrocarbons, halogenated hydrocarbons, ethers, ketones, alcohols and cellosolves. In particular, alcohol solvents such as methanol, ethanol and propanol and cellosolve solvents such as methylcellosolve and ethylcellosolve are preferred.

EXAMPLES

The following examples and comparative examples illustrate the present invention more specifically. These examples are, however, by no means limitative of the scope of the present invention.

Example 1

Synthesis of a Nonsolvate-Form Crystal of Polymethine Compound (X=Cl)

To 150 ml of acetone was added 15.45 g of polymethine ether compound represented by the formula (II) (R=CH$_3$), and 2.00 g of hydrogen chloride gas was blown into the mixture with stirring at 25-30° C. The resulting mixture was stirred at that temperature for 1 hour and then heated to the refluxing temperature, and 50 ml of ethyl acetate was added dropwise. After 1 hour of stirring at the same temperature, the mixture was cooled to 15-20° C. The resulting crystalline precipitate was collected by filtration, washed with ethyl acetate and then dried to give 14.65 g of a compound of formula (I) (X=Cl).

This crystalline compound showed a solubility of not lower than 25% in each of methanol and ethanol. The elemental analysis data, melting point (decomposition temperature), absorption maximum wavelength (λmax) and gram extinction coefficient (εg) of this crystalline compound were as follows.

| Elemental analysis (C$_{32}$H$_{36}$Cl$_2$N$_2$): MW = 519.6 | | | |
|---|---|---|---|
| | C | H | N |
| Calculated (%) | 73.98 | 6.98 | 5.39 |
| Found (%) | 73.51 | 6.86 | 5.43 |

Melting point (° C.): 212-217° C. (decomposition)
λmax: 783 nm (diacetone alcohol solution)
εg: 5.28 × 10$^5$ ml/g · cm A powder X-ray diffraction pattern of the crystalline compound obtained is shown in FIG. 1.

Figure 2:
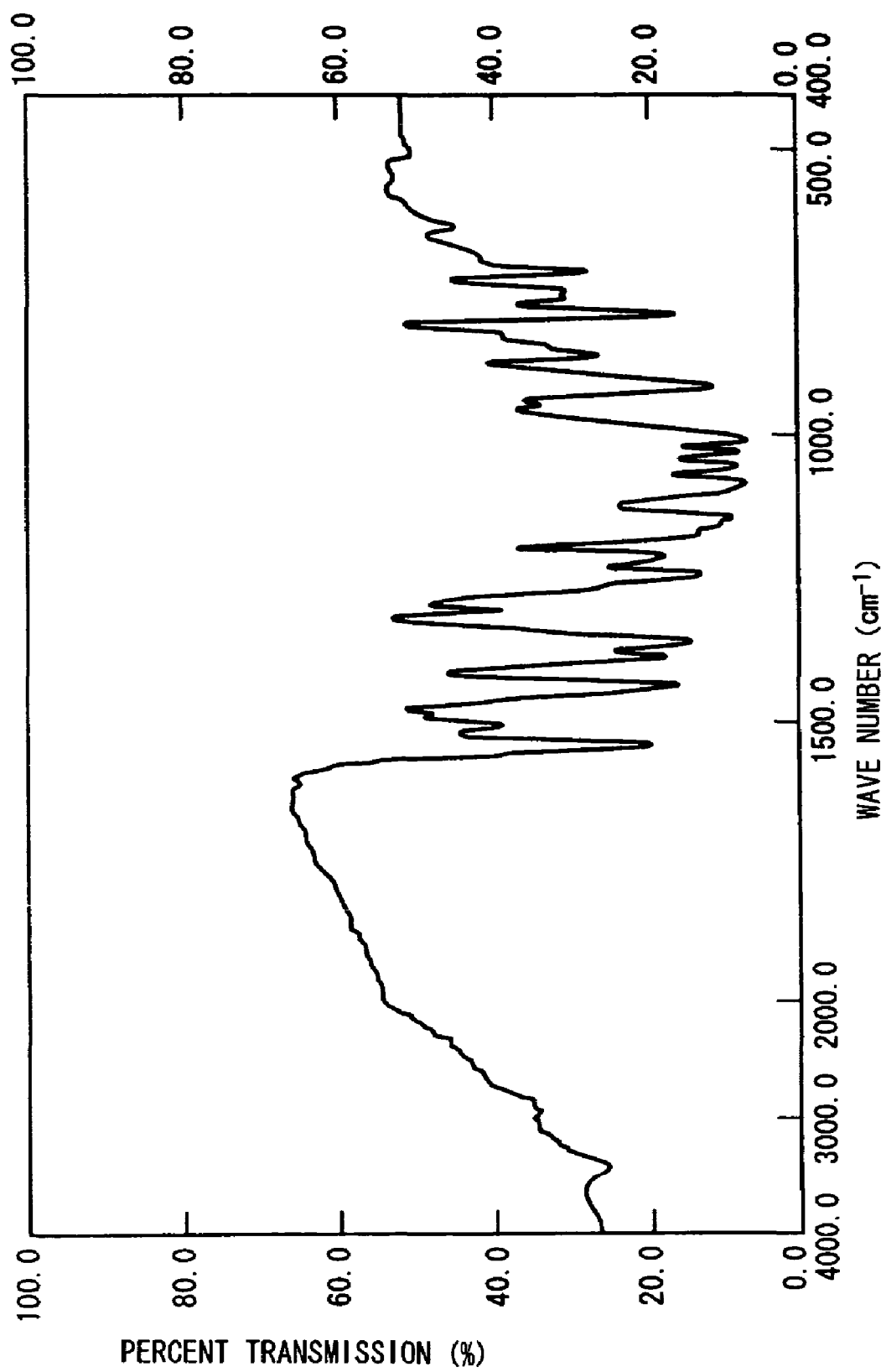
FIG. 2 is an IR absorption spectrum of the polymethine compound of Example 1.

An IR spectrum of the crystalline compound obtained is shown in FIG. 2.

Figure 3:
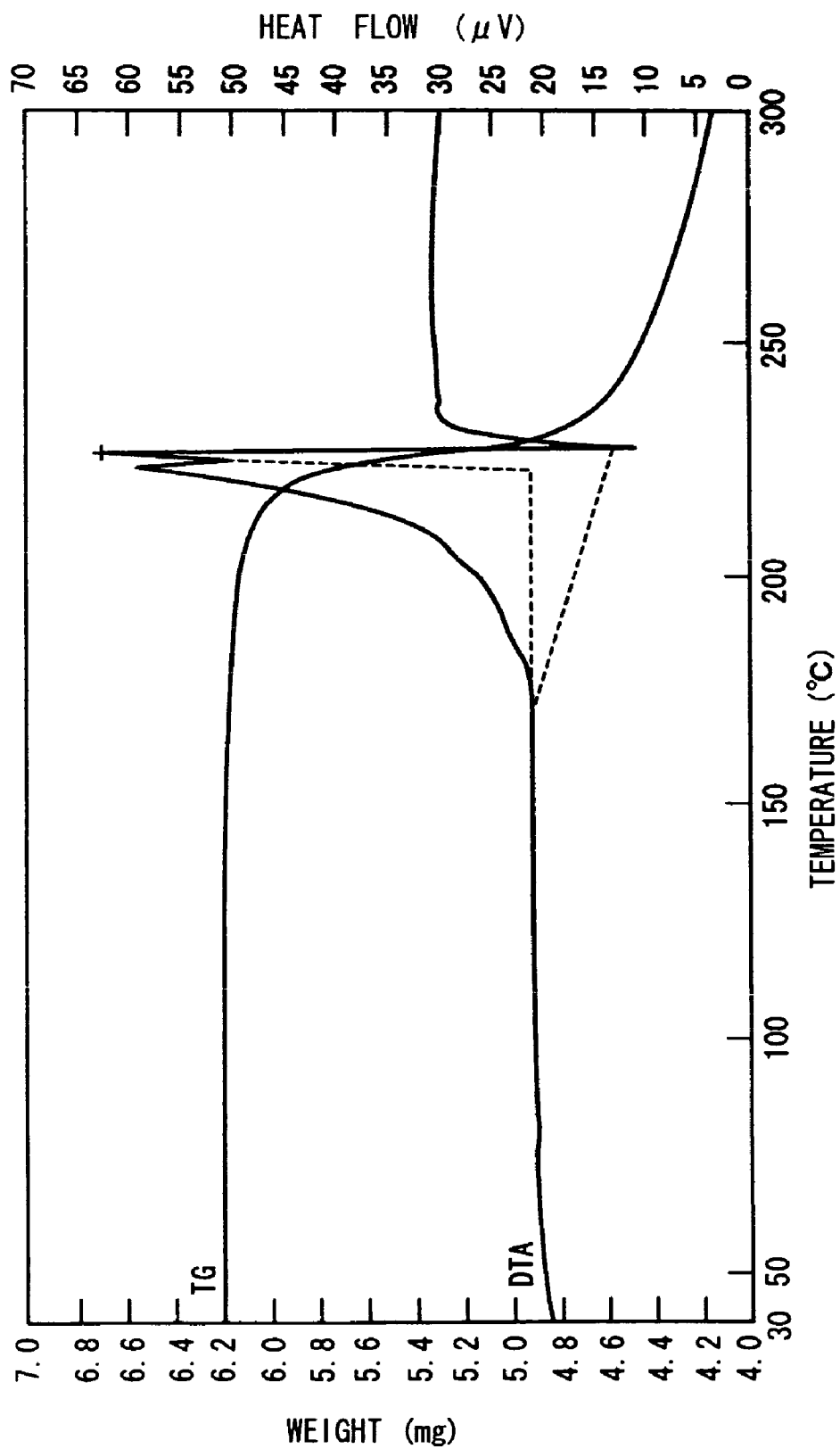
FIG. 3 is a TG-DTA (thermogravimetry-differential thermal analysis) chart of the polymethine compound of Example 1.

A TG-DTA (thermogravimetry-differential thermal analysis) chart of the crystalline compound obtained is shown in FIG. 3. The loss in weight as found by TG-DTA (not higher than 150° C.) was 0%. The stability of this crystalline compound in a mixed solvent (ethanol/methyl ethyl ketone=1/1) is shown in Table 1.

Example 2

Synthesis of a Nonsolvate-Form Crystal of Polymethine Compound (X=Br)

To 150 ml of acetone was added 15.45 g of a polymethine ether compound represented by the formula (II) (R=CH$_3$), and 5.60 g of 48% hydrobromic acid was added dropwise to the mixture with stirring at 25-30° C. The resulting mixture was stirred at that temperature for 1 hour and then heated to the refluxing temperature, and 50 ml of ethyl acetate was added dropwise. After 1 hour of stirring at the same temperature, the mixture was cooled to 15-20° C. The resulting crystalline precipitate was collected by filtration, washed with ethyl acetate and then dried to give 16.10 g of a compound of formula (I) (X=Br).

This crystalline compound showed a solubility of not lower than 25% in each of methanol and ethanol. The elemental analysis data, melting point (decomposition temperature), absorption maximum wavelength (λmax) and gram extinction coefficient (εg) of this crystalline compound were as follows.

| Elemental analysis (C$_{32}$H$_{36}$BrClN$_2$): MW = 564.0 | | | |
|---|---|---|---|
| | C | H | N |
| Calculated (%) | 68.15 | 6.43 | 4.97 |
| Found (%) | 68.01 | 6.51 | 4.93 |

Figure 4:
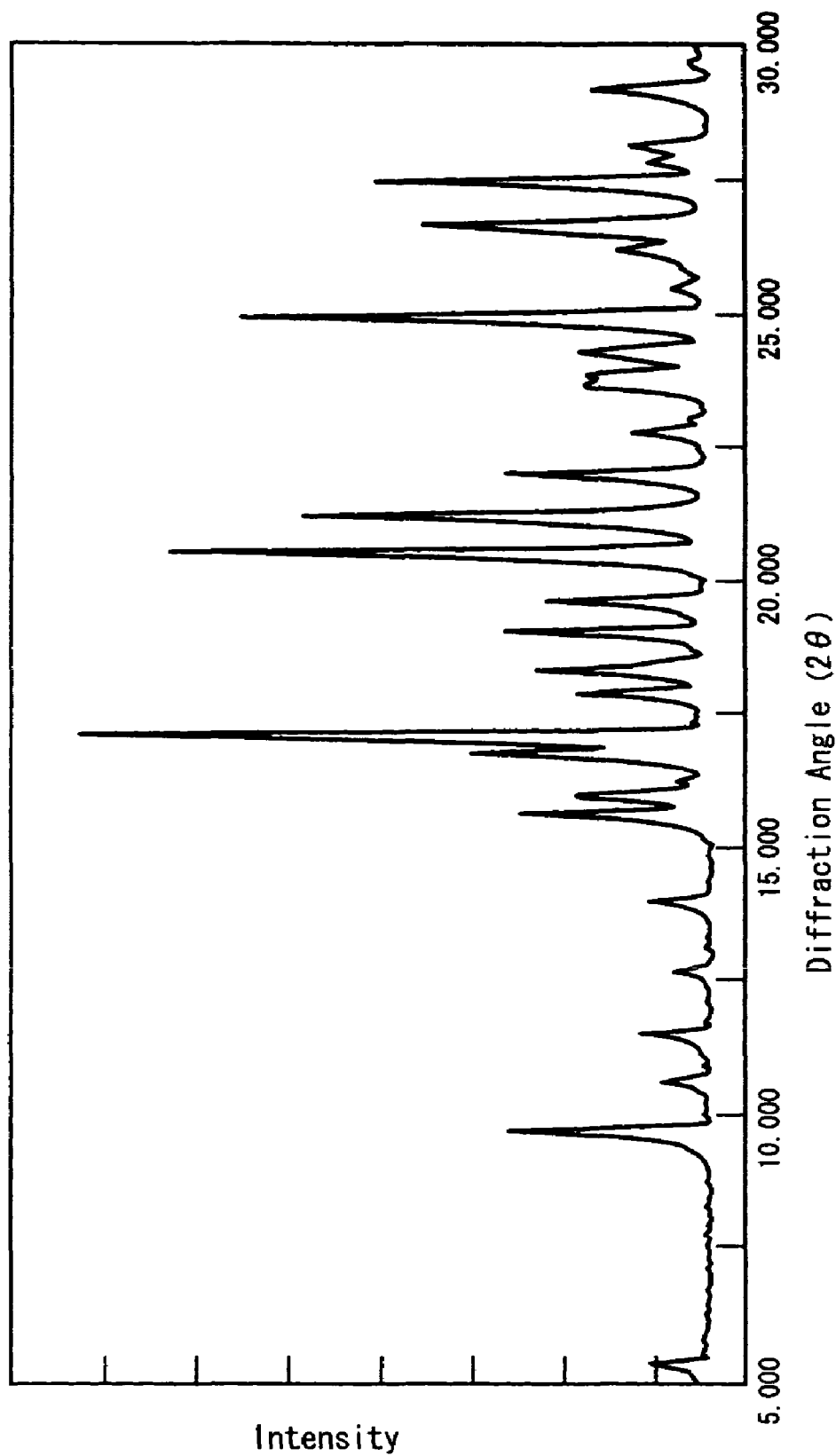
FIG. 4 is a powder X-ray diffraction pattern of the polymethine compound of Example 2.

Melting point (° C.): 225-230° C. (decomposition)
λmax: 783 nm (diacetone alcohol solution)
εg: 4.85 × 10$^5$ ml/g · cm A powder X-ray diffraction pattern of the crystalline compound obtained is shown in FIG. 4.

Figure 5:
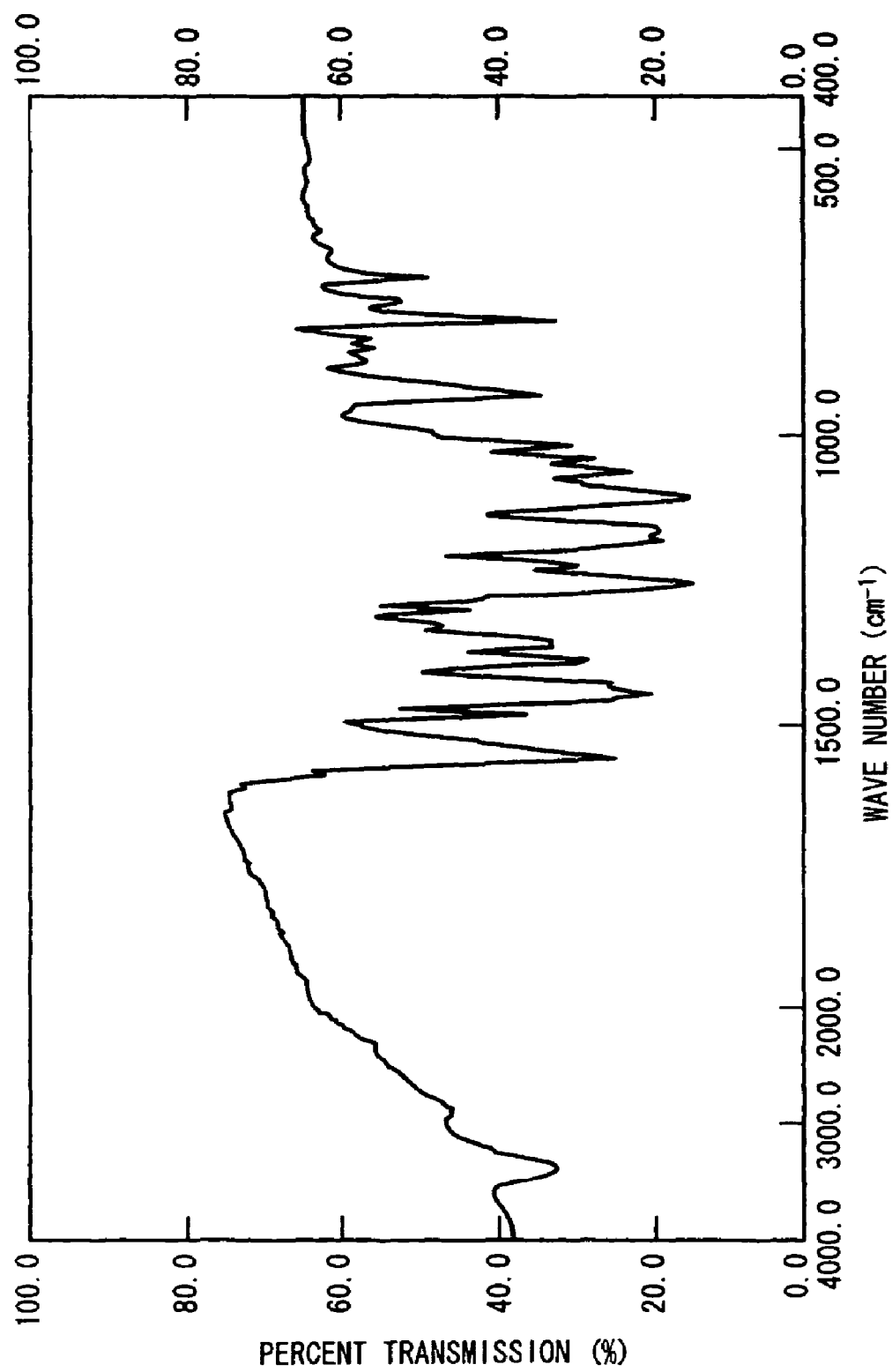
FIG. 5 is an IR absorption spectrum of the polymethine compound of Example 2.

An IR spectrum of the crystalline compound obtained is shown in FIG. 5.

Figure 6:
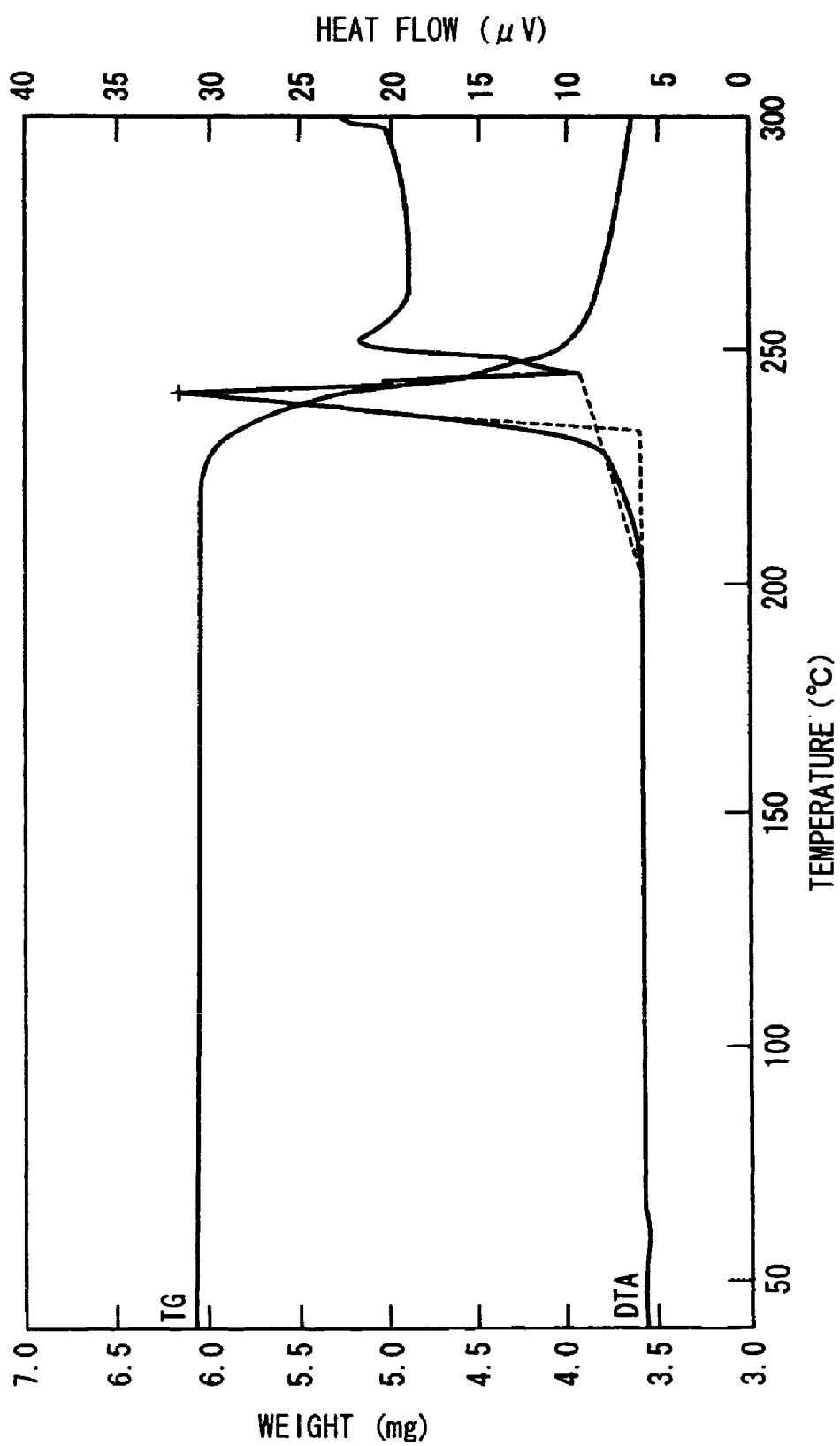
FIG. 6 is a TG-DTA (thermogravimetry-differential thermal analysis) chart of the polymethine compound of Example 2.

A TG-DTA (thermogravimetry-differential thermal analysis) chart of the crystalline compound obtained is shown in FIG. 6. The loss in weight as found by TG-DTA (not higher than 150° C.) was 0%. The stability of this crystalline compound in a mixed solvent (ethanol/methyl ethyl ketone=1/1) is shown in Table 1.

Example 3

Manufacture of a Near-Infrared Absorbing Material

A solution was prepared by dissolving 10 g of Delpet 80N (product of Asahi Chemical Industry; an acrylic resin) as a binder and 0.2 g of the crystalline compound of formula (I) (X=Cl) of the invention in 90 g of a mixed solvent composed of toluene/methyl ethyl ketone/methanol (1/1/0.1). This solution was applied, using a wire bar, to a polyethylene terephthalate (PET) film with an average thickness of 5 μm to a coat layer thickness, after drying, of about 5 μm. A near-infrared absorbing material specimen was thus obtained.

Laser beams emitted from a single-mode semiconductor laser (wavelength 830 nm) were condensed by means of a lens, and positions on the surface of the above specimen so that the beam diameter might amount to 10 μm. The semiconductor laser was adjusted so that the power of the laser beam arriving at the surface might be varied within the range of 50-200 mW, and the specimen was subjected to single pulse irradiation with a pulse width of 20 μs. After completion of irradiation, the specimen was observed under an optical microscope. It was confirmed that when the laser power arriving at the surface was 50 mW, a through hole with a diameter of about 10 μm was formed.

Example 4

Manufacture of a Near-Infrared Absorbing Material

A near-infrared absorbing material specimen was obtained in the same manner as in Example 3 except that 0.2 g of another compound of formula (I) (X=Br) according to the invention was used in lieu of 0.2 g of the crystalline compound of formula (I) (X=Cl) according to the invention.

Laser beams emitted from a single-mode semiconductor laser (wavelength 830 nm) were condensed by means of a lens, and positions on the surface of the above specimen so that the beam diameter might amount to 10 μm. The semiconductor laser was adjusted so that the power of the laser beam arriving at the surface might be varied within the range of 50-200 mW, and the specimen was subjected to single pulse irradiation with a pulse width of 20 μs. After completion of irradiation, the specimen was observed under an optical microscope. It was confirmed that when the laser power arriving at the surface was 50 mW, a through hole with a diameter of about 10 μm was formed.

Comparative Example 1

Commercial Polymethine Compound

A commercially available compound having the same chemical structure as that of the polymethine compound (X=Cl) of the present invention, which is found in Aldrich's Comprehensive Reagent Catalog (2003-2004 Japanese edition), was found to have the following melting point, absorption maximum wavelength (λmax) and gram extinction coefficient (εg).

Melting point (° C.): 187-198° C. (decomposition)

λmax: 783 nm (diacetone alcohol solution)

εg: $3.88 \times 10^5$ ml/g·cm

Figure 7:
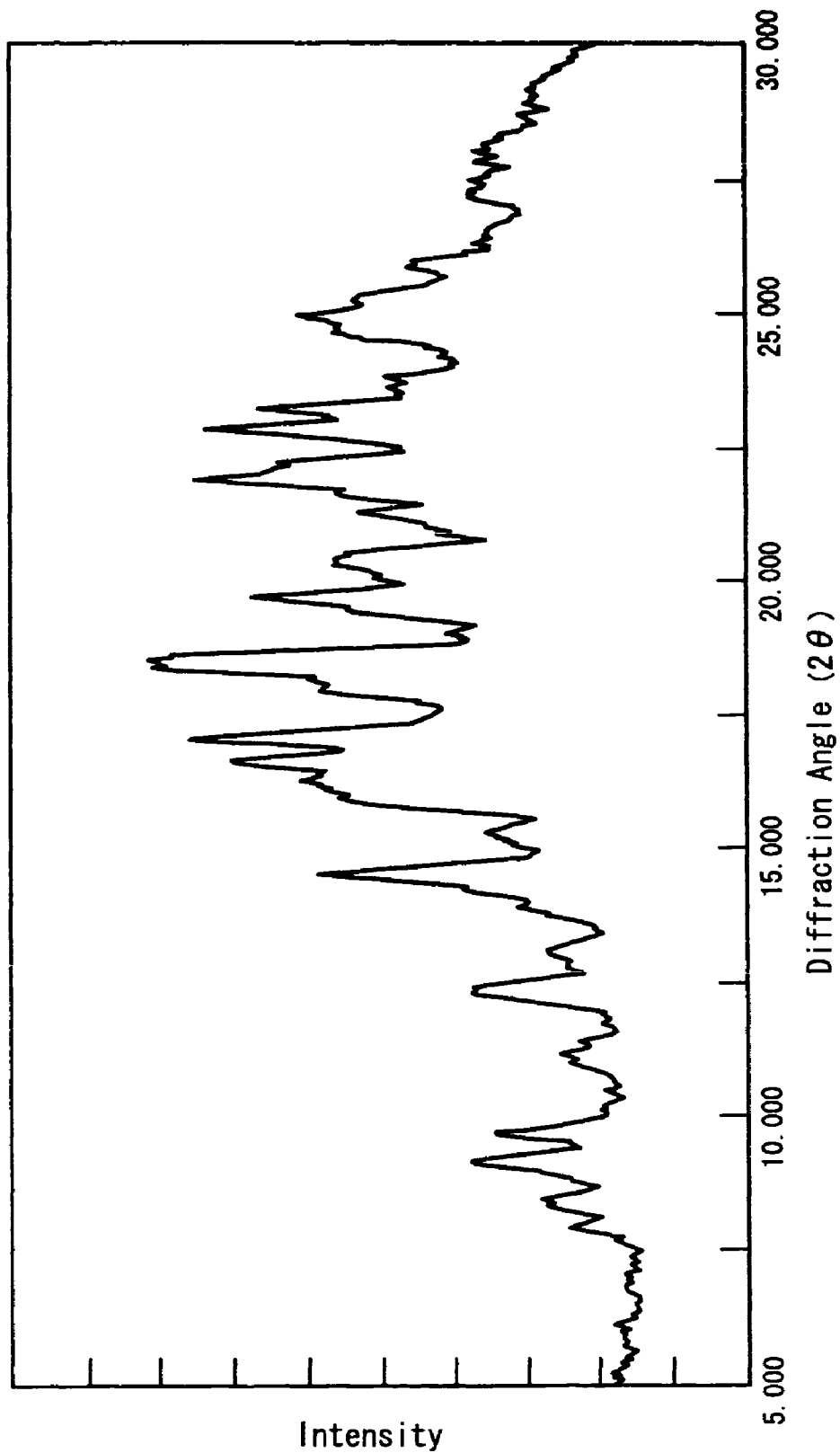
FIG. 7 is a powder X-ray diffraction pattern of the compound of Comparative Example 1.

A powder X-ray diffraction pattern of this compound is shown in FIG. 7.

Figure 8:
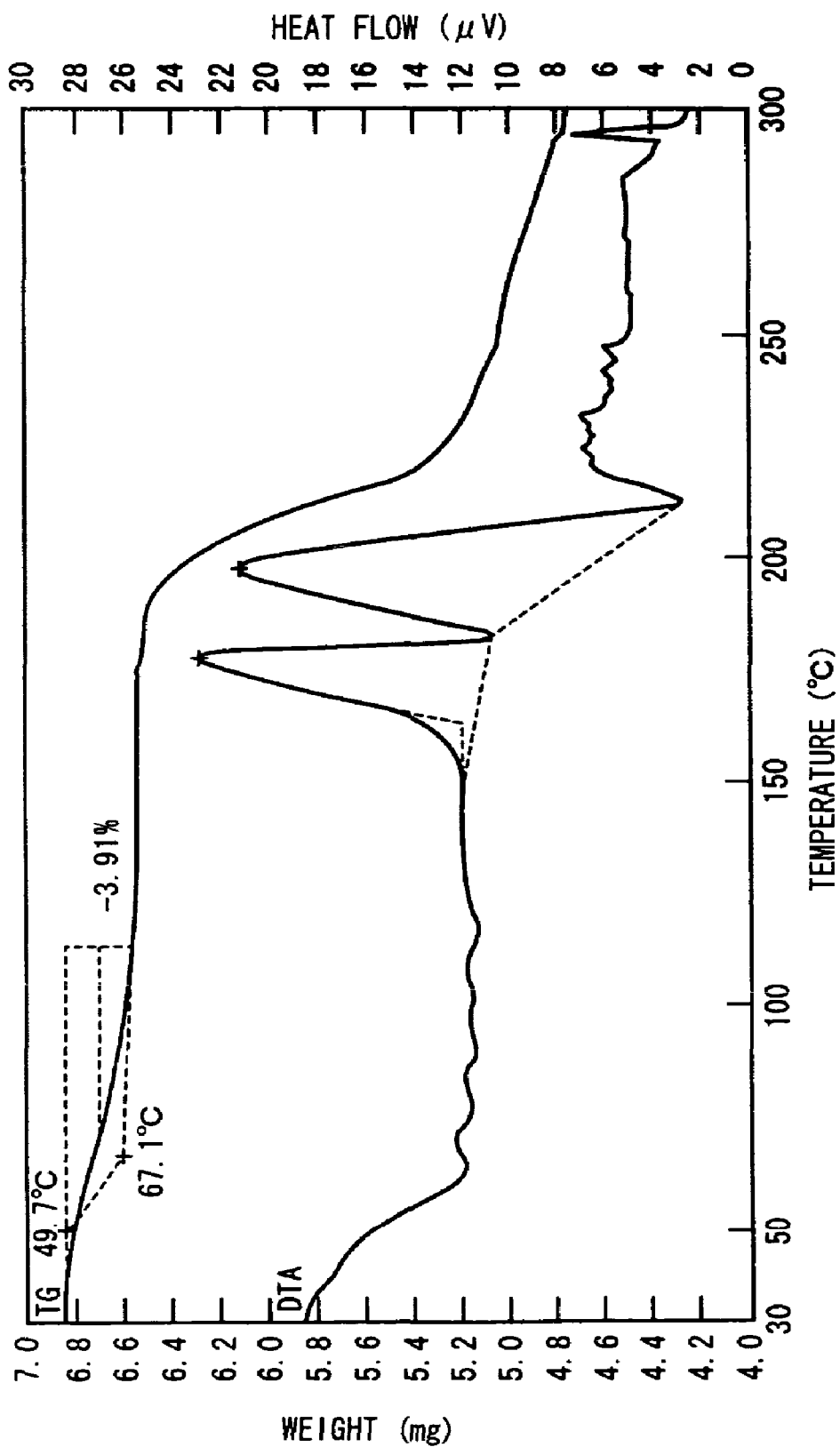
FIG. 8 is a TG-DTA (thermogravimetry-differential thermal analysis) chart of the compound of Comparative Example 1.

A TG-DTA (thermogravimetry-differential thermal analysis) chart of this compound is shown in FIG. 8. The loss in weight as found by TG-DTA (not higher than 150° C.) was about 3.9%.

The water content of this compound was determined on a Karl Fischer water-content meter. The water content was 3.7%. It was thus revealed that the weight loss mentioned above is due to this water and this compound is a hydrate.

The stability of this compound in a mixed solvent (ethanol/methyl ethyl ketone=1/1) is shown in Table 1.

Comparative Example 2

Synthesis of a Polymethine Compound (cf. WO 01/07524, Example 1 (b))

A diformyl compound represented by the formula (V) (n=2) (6.63 g) was added, at a temperature of 10° C. or below, to a mixture of 13.2 g of an indoline compound represented by the formula (IV) (R=CH$_3$), 60 ml of acetic anhydride, 9.6 ml of 48% hydrobromic acid and 6.25 g of sodium acetate. The resulting mixture was heated to 70° C. and stirred at that temperature for 1.5 hours. Then, after cooling to room temperature, 450 ml of water was added, and the whole mixture was stirred overnight. The resulting solid precipitate was collected by filtration, washed with water and dried at 60° C. A compound having the same basic structure as that of the compound of the present invention (X=Br) was obtained (13.21 g).

The melting point, absorption maximum wavelength (λmax) and gram extinction coefficient (εg) of the compound obtained were as follows.

Melting point (° C.): 212-218° C. (decomposition)

λmax: 783 nm (diacetone alcohol solution)

εg: $4.05 \times 10^5$ ml/g·cm

Figure 9:
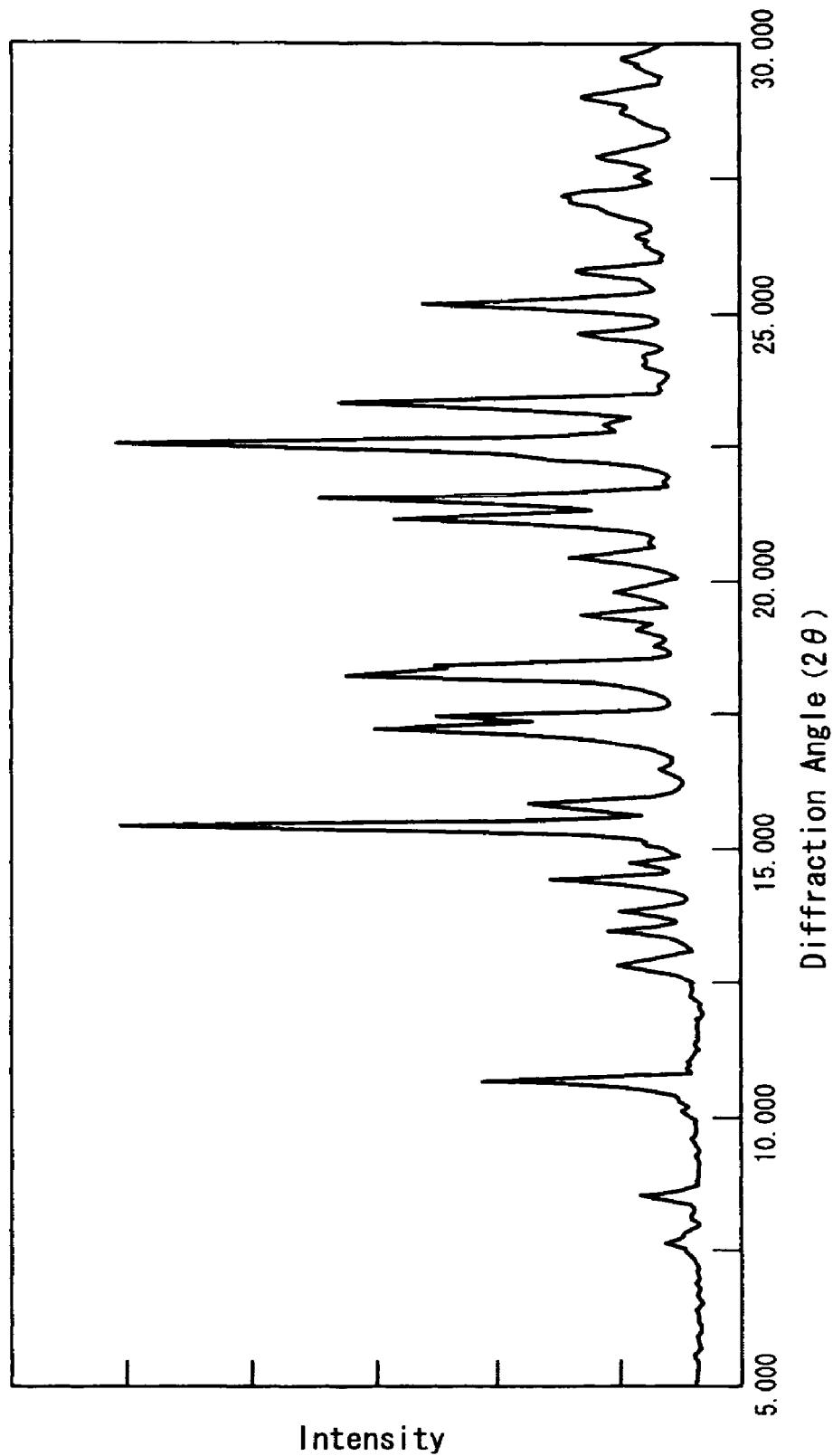
FIG. 9 is a powder X-ray diffraction pattern of compound of Comparative Example 2.

A powder X-ray diffraction pattern of the compound obtained is shown in FIG. 9.

Figure 10:
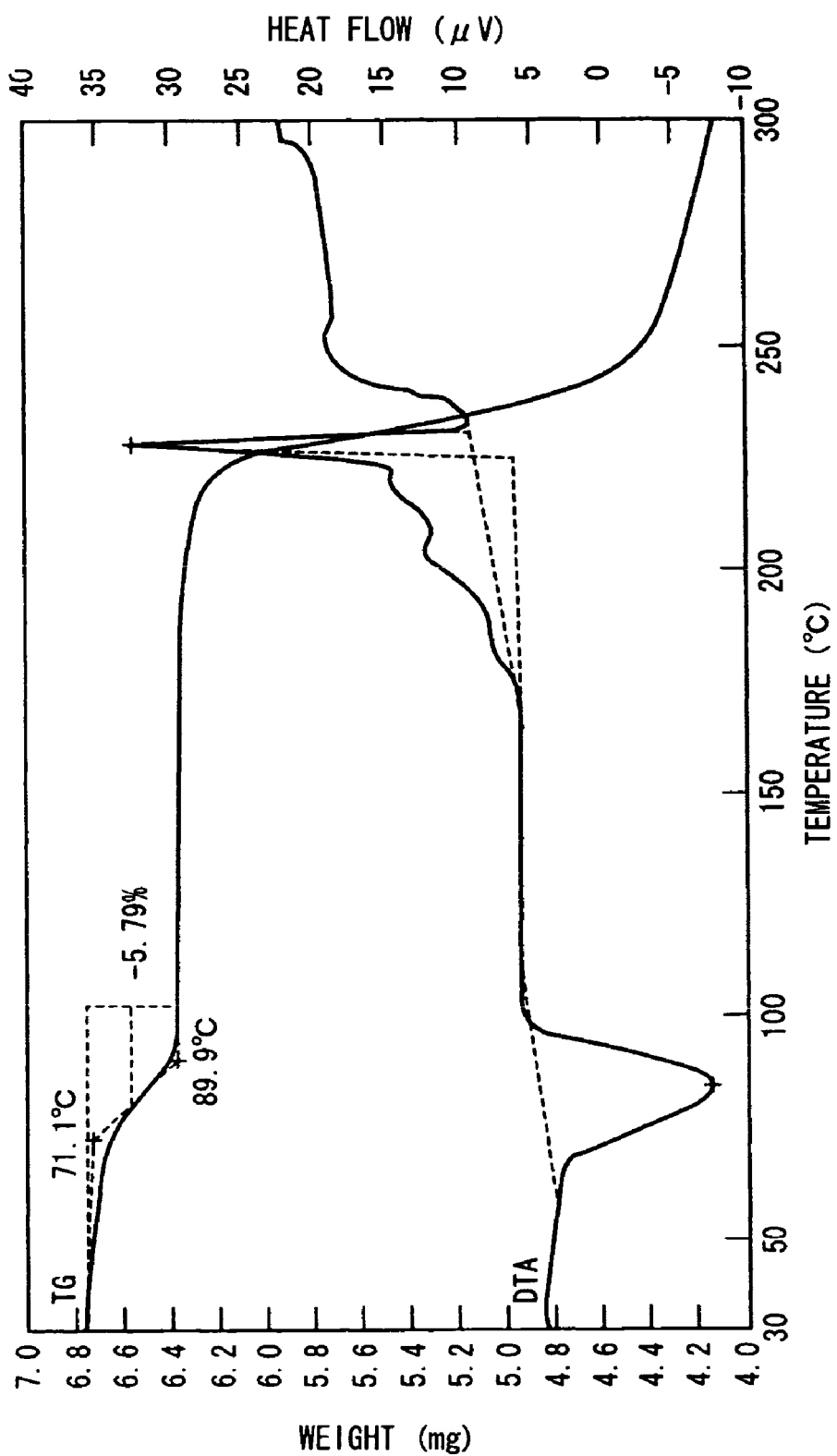
FIG. 10 is a TG-DTA (thermogravimetry-differential thermal analysis) chart of the compound of Comparative Example 2.

A TG-DTA (thermogravimetry-differential thermal analysis) chart of the compound obtained is shown in FIG. 10. The loss in weight as found by TG-DTA (not higher than 150° C.) was about 5.8%. The water content of this compound was determined using a Karl Fischer water-content meter. The water content was 5.6%. It was thus revealed that the weight loss is due to this water and this compound is a hydrate. The stability of this compound in a mixed solvent (ethanol/methyl ethyl ketone=1/1) is shown in Table 1.

<Stability in Solution>

In a solution stability test, each polymethine compound specified in below in Table 1 was dissolved in a mixture of ethanol and methyl ethyl ketone (1/1) to a concentration of 5% (w/v) and the solution was allowed to stand in a room (at room temperature) for about 10 days and, then, the absorbance (gram extinction coefficient) of the solution was measured for evaluation.

The decomposition percentage was calculated using the formula given below. The results thus obtained are shown in Table 1.

Decomposition percentage (%)=[(absorbance just after preparation of solution−absorbance after 10 days of standing)/absorbance just after preparation of solution]×100

TABLE 1

| Polymethine compound | % Decomposition |
| --- | --- |
| Example 1 | 0.8% |
| Example 2 | 0.6% |
| Comparative Example 1 | 3.9% |
| Comparative Example 2 | 5.1% |

In the case of preparing original plates for plate making or photoengraving, for instance, when the polymethine compound solution is poor in stability, the stock solution cannot be prepared in large amounts or cannot be stored, hence the production efficiency declines. Further, the decomposition of the polymethine compound, even if in a small percentage, may lead to changes in light-to-heat conversion efficiency or changes in color tone in original plates for photoengraving, which is unfavorable from the product quality viewpoint.

INDUSTRIAL APPLICABILITY

The nonsolvate-form crystal of polymethine compound of the invention is highly stable in solution and therefore is easy to handle. It has a high gram extinction coefficient and therefore is highly sensitive to general-purpose semiconductor lasers. Further, it is highly soluble in alcohol solvents. Thus, it is very useful in the fields of recording materials and plate making materials where laser beams are utilized.

The invention claimed is:

1. A nonsolvate-form crystal of a polymethine compound represented by the formula (I):

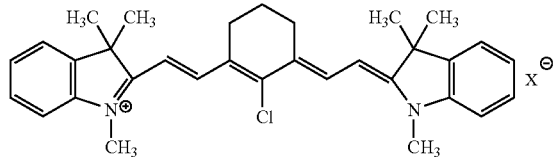

wherein X represents Cl or Br;

wherein in a TG-DTA (thermogravimetry-differential thermal analysis) chart of the compound, the weight loss in TG at 150° C. and below is not greater than 3%;

wherein if X is Cl then the melting point (decomposition temperature) thereof is not lower than 205° C., and the compound is characterized by a powder X-ray diffraction pattern showing characteristic peaks at diffraction angles (2θ±0.2°) of 11.2°, 16.7°, 24.2° and 25.3° in powder X-ray diffraction using the Cu-Kα rays; and wherein if X is Br then the melting point (decomposition temperature) thereof is not lower than 220° C., and the compound is characterized by a powder X-ray diffraction pattern showing characteristic peaks at diffraction angles (2θ±0.2°) of 17.0°, 20.5°, 21.1° and 24.9° in powder X-ray diffraction using the Cu-Kα rays.

2. A process for producing the nonsolvate-form crystal of a polymethine compound according to claim 1 which comprises reacting a polymethine ether compound represented by the formula (II) given below with hydrochloric acid or hydrobromic acid:

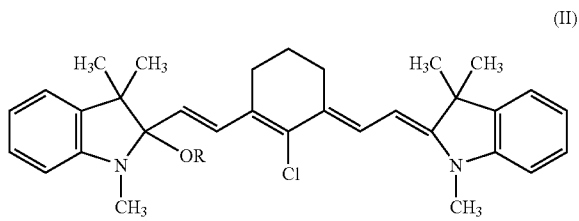

wherein R represents an alkyl group, an alkoxyalkyl group or an optionally substituted aryl group.

3. The method according to claim 2, wherein the compound produced is a nonsolvate-form crystal of a polymethine compound represented by the formula (I):

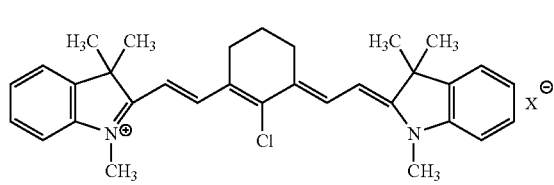

wherein X represents Cl or Br;

wherein in a TG-DTA (thermogravimetry-differential thermal analysis) chart of the compound, the weight loss in TG at 150° C. and below is not greater than 3%;

wherein if X is Cl then the melting point (decomposition temperature) thereof is not lower than 205° C., and the compound is characterized by a powder X-ray diffraction pattern showing characteristic peaks at diffraction angles (2θ±0.2°) of 11.2°, 16.7°, 24.2° and 25.3° in powder X-ray diffraction using the Cu-Kα rays; and wherein if X is Br then the melting point (decomposition temperature) thereof is not lower than 220° C., and the compound is characterized by a powder X-ray diffraction pattern showing characteristic peaks at diffraction angles (2θ±0.2°) of 17.0°, 20.5°, 21.1° and 24.9° in powder X-ray diffraction using the Cu-Kα rays.

4. The method according to claim 2, wherein R is a straight or branched alkyl group containing 1-8 carbon atoms; or an alkoxyalkyl group containing 2-8 carbon atoms; or a phenyl group or naplithyl group optionally substituted with a substituent selected from the group consisting of an alkyl group containing 1-4 carbon atoms, an alkoxy group containing 1-4 carbon atoms, an amino group, a nitro group, a hydroxy group and a halogen atom.

5. The method according to claim 2, wherein R is an alkyl group containing 1-8 carbon atoms, an alkoxyalkyl group containing 2-4 carbon atoms, a phenyl group, an alkyl-substituted phenyl group or an alkoxy-substituted phenyl group.

6. A near-infrared absorbing material, characterized in that it comprises the nonsolvate-form crystal of a polymethine compound according to claim 1.

7. A nonsolvate-form crystal of a polymethine compound represented by the formula (I):

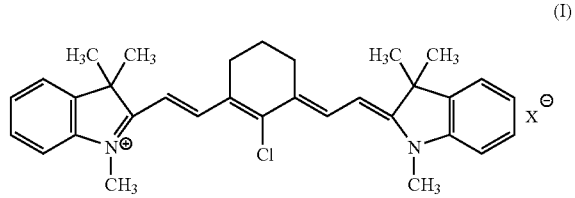

wherein X represents Cl or Br, which is produced according to a process which comprises reacting a polymethine ether compound represented by the formula (II) given below with hydrochloric acid or hydrobromic acid:

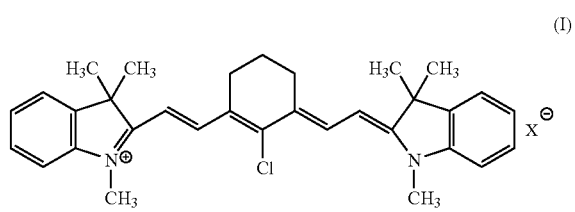

wherein R represents an alkyl group, an alkoxyalkyl group or an optionally substituted aryl group.

8. The compound according to claim 7, wherein the compound of formula (I) is a nonsolvate-form crystal of a polymethine compound represented by the formula (I):

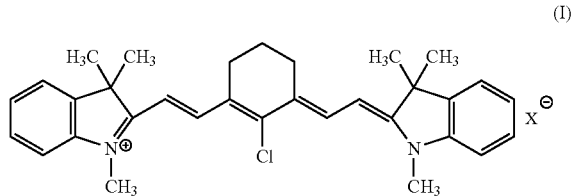 (I)

wherein X represents Cl or Br;
wherein in a TG-DTA (thermogravimetry-differential thermal analysis) chart of the compound, the weight loss in TG at 150° C. and below is not greater than 3%;
wherein if X is Cl then the melting point (decomposition temperature) thereof is not lower than 205° C., and the compound is characterized by a powder X-ray diffraction pattern showing characteristic peaks at diffraction angles (2θ±0.2°) of 11.2°, 16.7°, 24.2° and 25.3° in powder X-ray diffraction using the Cu-Kα rays; and
wherein if X is Br then the melting point (decomposition temperature) thereof is not lower than 220° C., and the compound is characterized by a powder X-ray diffraction pattern showing characteristic peaks at diffraction angles (2θ±0.2°) of 17.0°, 20.5°, 21.1° and 24.9° in powder X-ray diffraction using the Cu-Kα rays.

9. The compound according to claim 7, wherein R is a straight or branched alkyl group containing 1-8 carbon atoms; or an alkoxyalkyl group containing 2-8 carbon atoms; or a phenyl group or naplithyl group optionally substituted with a substituent selected from the group consisting of an alkyl group containing 1-4 carbon atoms, an alkoxy group containing 1-4 carbon atoms, an amino group, a nitro group, a hydroxy group and a halogen atom.

10. The compound according to claim 7, wherein R is an alkyl group containing 1-8 carbon atoms, an alkoxyalkyl group containing 2-4 carbon atoms, a phenyl group, an alkyl-substituted phenyl group or an alkoxy-substituted phenyl group.

* * * * *